(12) United States Patent
Loccufier et al.

(10) Patent No.: US 6,566,034 B2
(45) Date of Patent: *May 20, 2003

(54) PHOTOGRAPHIC MATERIAL CONTAINING A NOVEL HYDRAZINE TYPE

(75) Inventors: Johan Loccufier, Zwijnaarde (BE); Stefaan Lingier, Assenede (BE)

(73) Assignee: AGFA-Gevaert, Mortsel (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/948,929

(22) Filed: Sep. 7, 2001

(65) Prior Publication Data

US 2002/0058195 A1 May 16, 2002

Related U.S. Application Data

(60) Provisional application No. 60/243,991, filed on Oct. 27, 2000.

(30) Foreign Application Priority Data

Sep. 11, 2000 (EP) .............................................. 00203065

(51) Int. Cl.$^7$ ................................................. G03C 1/06
(52) U.S. Cl. ........................ 430/264; 430/598; 430/607
(58) Field of Search ................................. 430/264, 598, 430/607

(56) References Cited

U.S. PATENT DOCUMENTS

| | | | | | |
|---|---|---|---|---|---|
| 4,891,304 | A | * | 1/1990 | Nakamura | 430/448 |
| 5,631,125 | A | * | 5/1997 | Dewanckele et al. | 430/564 |
| 5,989,774 | A | * | 11/1999 | Loccufier et al. | 430/264 |
| 5,998,087 | A | * | 12/1999 | Loccufier et al. | 430/264 |
| 6,355,394 | B1 | * | 3/2002 | Loccufier et al. | 430/264 |
| 6,361,920 | B1 | * | 3/2002 | Loccufier et al. | 430/264 |

FOREIGN PATENT DOCUMENTS

| | | |
|---|---|---|
| EP | 0 435 333 A | 7/1991 |
| EP | 0 816 913 A | 1/1998 |
| GB | 2 297 747 A | 8/1996 |

* cited by examiner

*Primary Examiner*—Geraldine Letscher
(74) *Attorney, Agent, or Firm*—Joseph T. Guy; Nexsen Pruet Jacobs & Pollard, LLC

(57) ABSTRACT

A high contrast photographic material is disclosed containing a new type of hydrazine compound characterized in that said hydrazine compound comprises a redox moiety capable of developing an exposed silver halide crystal.

Preferably the photographic material is a graphic arts material for pre-press applications. The developed photographic material shows high gradation, and excellent dot quality and exposure latitude.

5 Claims, No Drawings

PHOTOGRAPHIC MATERIAL CONTAINING A NOVEL HYDRAZINE TYPE

This application claims the benefit of U.S. Provisional application Ser. No. 60/243,991, filed Oct. 27, 2000.

FIELD OF THE INVENTION

The present invention relates to a high contrast photographic material containing a novel type of nucleating agent.

BACKGROUND OF THE INVENTION

In graphic arts reproduction processes the original image appearing to have a continuous tone gradation is reproduced by a collection of a large number of dots and/or lines, either by optical means in the case of a camera film, or by electronic means in case of a recorder film. The tone of the reproduced image is influenced by both the size of the dots and lines and their density. A graphic arts film exposed in a way to exactly render the relative proportions of black and white in the original must produce dots and lines of sufficient density; another reason herefore is the fact that no substantial amount of copying light may be transmitted through the dots and lines in a further duplicating cycle or during the direct exposure of a printing plate. Therefore a photographic element showing high contrast or so-called "lith gradation" on development is highly desired. Furthermore the generated or reproduced dots and lines must exhibit a well-shaped form and sharp edges.

This most desired combination of high contrast and excellent dot quality is commonly termed "lith quality". The goal of achieving optimal lith quality is reached by the combination of specially designed graphic arts material and appropriate processing systems. A first group of such processing systems consists of the traditional "lith developers" characterized by the presence of hydroquinone as the sole developing agent and a low but critical sulphite ions content giving rise to an infectious development mechanism, as was described by Yule in *The Journal of the Franklin Institute*, Vol. 239, p. 221–223, (1945). This type of development is believed to proceed autocatalytically. The low concentration of sulphite is maintained by the progressive dissociation of an aldehyde-bisulphite adduct. However these conventional lith developers are rather instable in time and require complicated replenishment systems for both oxidation and exhaustion. Furthermore their developing capacity is limited due to the fact that they contain hydroquinone as the sole developing agent.

In more recent times so-called "hard dot Rapid Access" developers were introduced on the market which combine a good stability with a "lith quality" in the reproduction of lines and screen dots. Examples of such developers and corresponding appropriate photographic materials include the GRANDEX system, marketed by FUJI PHOTO ltd., AGFASTAR, marketed by AGFA-GEVAERT N.V. and the ULTRATEC system, marketed by EASTMAN KODAK Co. Some of these systems make use of the contrast promoting action, induced by a nucleating mechanism, of hydrazine derivatives known for long time in the photographic art. As described by Simson et al., U.S. Pat. No. 4,650,746, use of a hydrazine compound permits the use of an auxiliary development agent in combination with the hydroquinone type of developing agent so that the development capacity can be increased. It also permits the presence of a relatively high sulphite concentration in order to protect the developer against aerial oxidation and thereby prolonging its effective working life. Further early disclosures on hydrazine compounds, incorporated either in a photographic element or in a developing solution, include Smith U.S. Pat. Nos. 2,410,690, Stauffer 2,419,974, Trivelli 2,419,975 and Hunsberger 2,892,715 and an article by Stauffer, Smith and Trivelli entitled "The influence of photographic developers containing hydrazine upon the characteristic curves of photographic materials", *The Journal of the Franklin Institute*, Vol. 238, p. 291–298, October 1944. Since then the photographic world has undertaken extensive research on hydrazine chemistry for use in photographic applications and the recent patent literature on new hydrazine derivatives and on the combination of known or new hydrazines with other useful ingredients in photographic elements or developers is abundant.

A practical early recognized problem was caused by the high pH levels needed for the developers containing hydrazine compounds or used with photographic elements containing these compounds in order to get the maximum effect on contrast. The teaching of Nothnagle U.S. Pat. No. 4,269,929 brought a solution to this problem. Here a method for high contrast development was disclosed involving a hydrazine compound, either in the photographic element or in the developer, said developer further containing a hydroquinone developing agent, a 3-pyrazolidinone developing agent, sulphite ions, and a "contrast-promoting amount" of an amino compound. In a preferred embodiment the hydrazine compound was incorporated in the photographic material. According to this patent, issued May 26, 1981, this particular combination of ingredients allow the use of a rather moderate alkaline pH for the developing solution while retaining the desired high contrast and dot quality characteristics. In this way an excellent combination of lith quality of the finished material, high developing capacity and long effective life of the developer was achieved.

Since then intense research has been conducted to improve the performance of hydrazines, mostly acylhydrazides, and in particular to make them workable in combination with conventional rapid access developers having a pH around 10.5 and containing no special ingredients such as amine boosters. Specific new hydrazide derivatives are described, e.g. in JP-A 57-99635, EP 0 217 310, JP-A 61-270744, JP-A 62-89958, EP 0 283 040, EP 0 301 799, U.S. Pat. No. 4,816,373, 4,847,180, JP-A 63-294552, JP-A 63-44649, JP-A 63-8715, EP 0 283 040, JP-A 01-100530, EP 0 345 025, JP-A 01-201650, EP 0 356 898, DE 38 29 078, U.S. Pat. Nos. 4,950,578, 5,028,510, EP 0 399 460, U.S. Pat. No. 5,006,445, JP-A 01-285940, U.S. Pat. Nos. 4,988,604, 4,994,365, JP-A 02-300474, JP-A 02-302750, JP-A 02-841, JP-A 02-947, EP 0 444 506, EP 0 479 156, JP-A 04-283743, EP 0 539 925, U.S. Pat. No. 5,212,045, EP 0 569 983, U.S. Pat. Nos. 5,284,732, 5,447,820, 5,424,170, EP 0 671 654, WO 95/32452, WO 95/32453, DE 19522725, EP 0 713 130, U.S. Pat. No. 5,451,486, EP 0 731 385, EP 0 736 798, EP 0 763 771, EP 0 782 041, EP 0 782 042, U.S. Pat. Nos. 5,686,222, 5,858,610, 5,702,866, and GB 2 297 747.

A study on the nucleating mechanism of acylhydrazides, responsible for infectious development, can be find in Simson, *SPSE*, 25th Fall Symposium, (1985), p. 48. Other studies include Kitchin et al., *J. Phot. Sci.*, Vol. 35, (1987), p. 162, Shinoara et al., *J. Photogr. Sci.*, Vol. 35, (1987), p. 181, Kobayashi, *J. Phot. Sci.*, Vol. 43, (1995), p. 186, and Yamada, *J. Imag. Sci. Techn.*, Vol. 43, No. 1, (1999), p. 103.

An important technological breakthrough was the development and use of sulphonamido-arylhydrazides as disclosed in EP 0 286 840 and U.S. Pat. No. 5,104,769, which proved to be a very reactive and effective type. Another main progress was the use of hydrazides, especially sulphonamido-arylhydrazides in combination with so-called "incorporated boosters", such as disclosed in Machonkin U.S. Pat. No. 4,975,354, which can be incorporated into the photographic material itself instead of the developer. Still other graphic arts systems are based on the use of hydrazine types that can release a photographically useful group, e.g. an accelerator or a development restrainer, such as disclosed in e.g. EP 0 393 720, EP 0 393 721, EP 0 399 460, U.S. Pat. No. 5,258,259, EP 0 420 005, U.S. Pat. Nos. 5,252,438 and 5,262,274.

In EP 0 816 913 a new class of active arylhydrazides is disclosed having in ortho position a substituent comprising a pyridinium, quinolinium or isoquinolinium group. With this class of hydrazides high gradation was obtained. According to a further improvement on this class of compounds disclosed in EP 0 902 319 the pyridinium, quinolinium or isoquinolinium group is substituted by an aliphatic chain comprising at least one carbon—carbon triple bond.

Still further variants of the hydrazide class of EP 0 816 913 are disclosed in pending European patent applications appl. Nos. 99203010 and 99203011.

The present invention extends the teachings on hydrazine compounds in photographic silver halide materials, and constitutes a further improvement to the teachings of EP 0 816 913, EP 0 902 319, and appl. Nos. 99203010 and 99203011 cited above.

OBJECTS OF THE INVENTION

It is an object of the present invention to provide a new class of active hydrazide nucleating agents for use in high contrast photographic materials.

It is a further object of the present invention to provide photographic materials for graphic arts applications with improved gradation, image quality and exposure latitude.

SUMMARY OF THE INVENTION

The objects of the present invention are realised by providing a photographic material comprising a support and at least one silver halide emulsion layer characterized in that said photographic material contains a hydrazine compound represented by general formula (I)

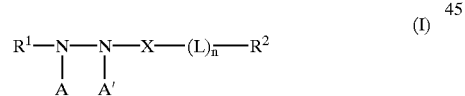

(I)

wherein:
—$R^1$ is represented by:

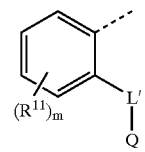

wherein:
$R^{11}$ represents any substituent,
m represents an integer from 0 to 4,
L' represents a divalent linking group,
Q represents a cationic aromatic nitrogen containing heterocycle.
$R^2$ is selected from the group consisting of a substituted or unsubstituted, saturated or unsaturated aliphatic chain, a substituted or unsubstituted aryl or heteroaryl, with the proviso that $R^2$ comprises a redox moiety, capable of developing an exposed silver halide crystal,
X is selected from the group consisting of —CO—, —SO—, —SO$_2$—, —CO—CO—, —P(O)R$^3$, —C(=N—R$^4$), wherein each of $R^3$ and $R^4$ is independently selected from hydrogen, a substituted or unsubstituted, saturated or unsaturated aliphatic chain, a substituted or unsubstituted aryl or heteroaryl, OR$^5$, NR$^6$R$^7$; each of $R^5$ to $R^7$ is selected from the group consisting of hydrogen, a substituted or unsubstituted, saturated or unsaturated aliphatic chain, and a substituted or unsubstituted aryl or heteroaryl,
L is a divalent linking group,
n=0 or 1,
each of A and A' independendently represents a hydrogen, a group capable of yielding a hydrogen under alkaline photographic processing conditions or a SO$_2$R$^8$-group provided that if A is SO$_2$R$^8$ A' is a hydrogen and vice versa; $R^8$ is selected from the group consisting of a substituted or unsubstituted, saturated or unsaturated aliphatic chain, a substituted or unsubstituted aryl or heteroaryl.

In a preferred embodiment the photographic material is developed in an ascorbic acid developer.

DETAILED DESCRIPTION OF THE INVENTION

Typical hydrazine compounds according to the present invention are given below. Preferred redox moieties are hydroquinone and catechol moieties.

| Structure | Compound |
|---|---|
| 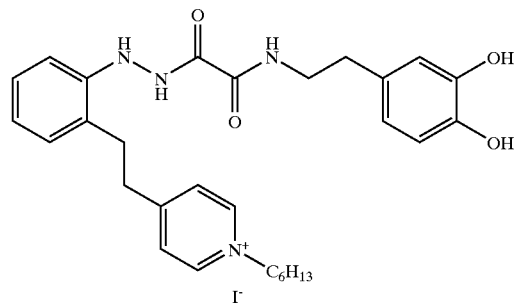 | 1 |

-continued

| Structure | Compound |
|---|---|
| (structure) | 2 |
| (structure) | 3 |
| (structure) | 4 |
| (structure) | 5 |
| (structure) | 6 |

| Structure | Compound |
|---|---|
| 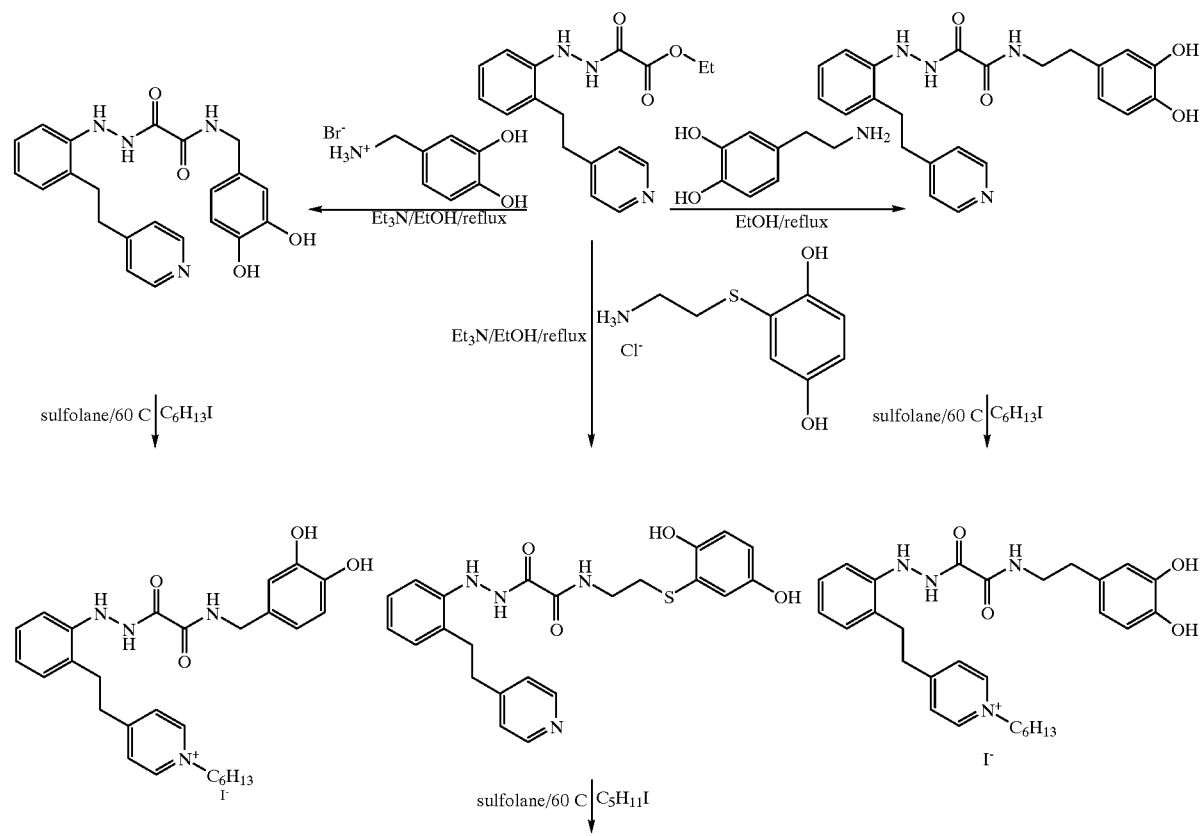 | 7 |
| 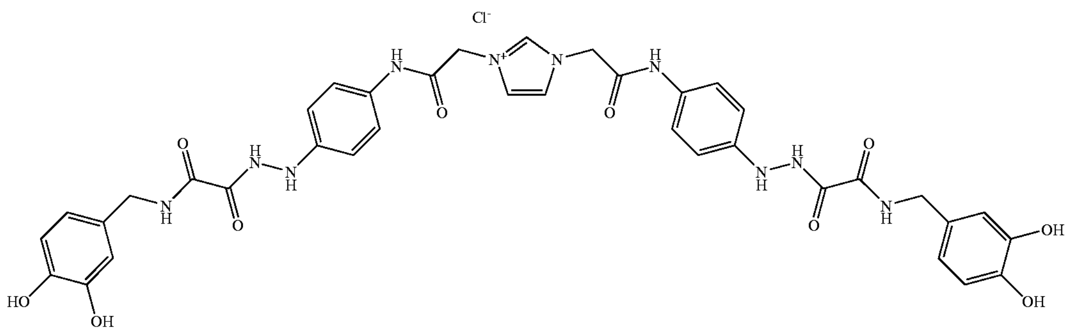 | 8 |
The hydrazides are prepared according to well known synthetic procedures. The synthesis of some examples will be briefly described.
General synthetic scheme for compounds 1 to 3:

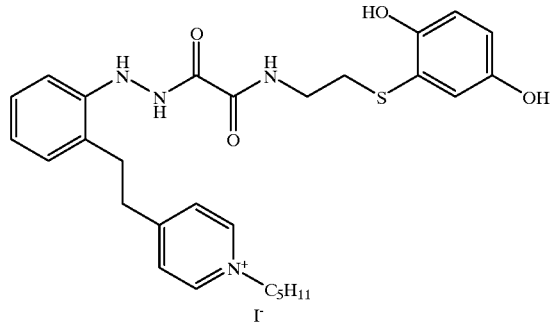

The synthesis of compound 1 and 3 is straightforward from commercial available compounds, according to earlier reported procedures. The synthesis of compound 2 is more troublesome and will be described more in detail.

The Synthesis of the Amino-Hydroquinone:

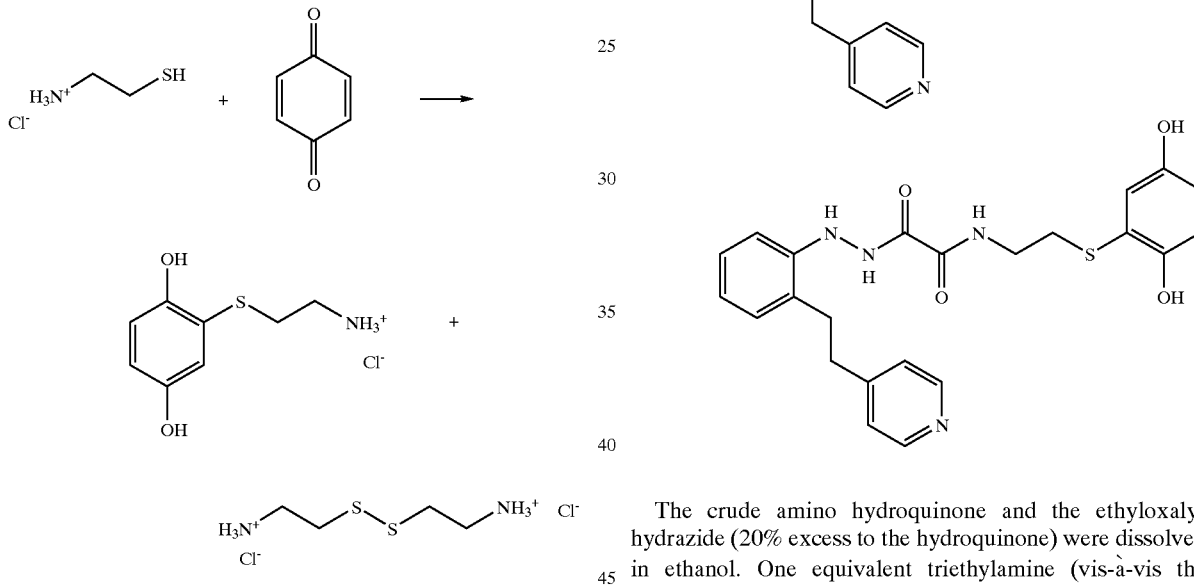

A solution of 5.7 g (0.05 mol) of cysteamine chlorohydrate in methanol was added to a suspension of 5.4 g (0.05 mol) of benzoquinone in 25 ml of methanol. The temperature was kept at 25° C., and the mixture was stirred for 24 hours at room temperature. The precipitated disulfide was removed by filtration and the methanol solution of the crude hydroquinone was concentrated under reduced pressure. The crude hydroquinone was used without purification.

The Preparation of the Intermediate Oxalyl Amide Hydrazide

The crude amino hydroquinone and the ethyloxalyl hydrazide (20% excess to the hydroquinone) were dissolved in ethanol. One equivalent triethylamine (vis-à-vis the hydroquinone) was added and the mixture was refluxed for 2 hours. The excess of hydrazide was removed by filtration and the ethanol was concentrated under reduced pressure. The oxalyl amide hydrazide was isolated by preparative column chromatography. (Kromasil 60 Å 10μ, eluent $CH_2Cl_2$/MeOH 93/7)

The Preparation of Compound 2

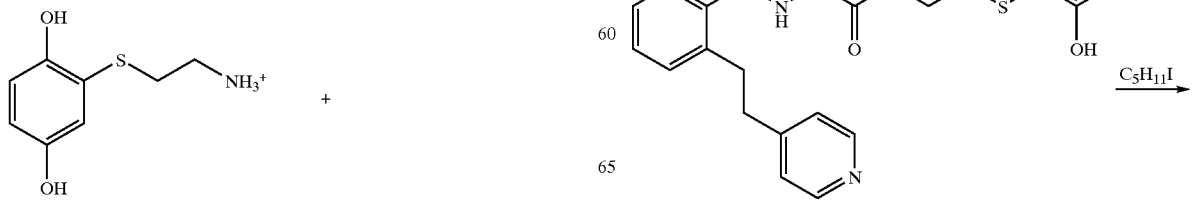

-continued

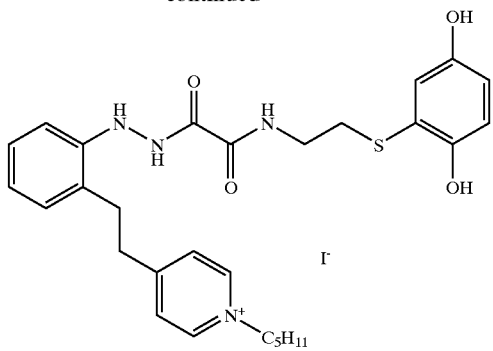

2.6 g (5.5 mmol) of the intermediate pyridyl hydrazide was suspended in 25 ml of sulfolane. 1.4 g (6.6 mmol) of pentyliodide in 5 ml sulfolane was added, and the mixture was heated to 75° C. for two and a half hours. The reaction mixture was pourred into 200 ml of ethyl acetate/methyl t.-butyl ether 1/1. The solvent was decanted and the oily residue was treated with 150 ml of methyl t.-butyl ether/ ethyl acetate 1/2. The oily residue solidified slowly and compound 2 was isolated by filtration. Compound 2 was treated with 50 ml of i.-propyl acetate, isolated by filtration and dried.

Having described the novel class of hydrazide compounds and their preparation we will now describe the photographic material in which these compounds are incorporated as nucleating agents.

The hydrazides used in accordance with the present invention can be incorporated as organic solvent solutions, preferably as methanolic solution.

The nucleating hydrazine compounds of the present invention can be incorporated into the emulsion layer but, alternatively, they can be present in an adjacent hydrophylic layer.

Suitable organic resin supports for use in accordance with the present invention include cellulose nitrate film, cellulose acetate film, poly(vinyl acetal) film, polystyrene film, poly (ethylene terephthalate) film, polycarbonate film, polyvinylchloride film or polyolefin films such as polyethylene or polypropylene film. The thickness of such organic resin film is preferably comprised between 0.025 and 0.25 mm.

In a most preferred embodiment the support is a polyethylene terephthalate support, optionally provided with a subbing layer. An example of a suitable subbing layer is a layer containing a polymer containing covalently bound chlorine. Suitable chlorine containing polymers are e.g. polyvinyl chloride, polyvinylidene chloride, a copolymer of vinylidene chloride, an acrylic ester and itaconic acid, a copolymer of vinyl chloride and vinylidene chloride, a copolymer of vinyl chloride, vinylidene chloride and itaconic acid, a copolymer of vinyl chloride, vinyl acetate and vinyl alcohol, A preferred chlorine containing polymer is co(vinylidenechloride-methylacrylate-itaconic acid; 88%/ 10%/2%). A most suitable subbing layer contains the latter polymer and a colloidal silica such as KIESELSOL 100F (Bayer AG). Optionally to this composition can be added co(methylacrylate-butadiene-itaconic acid) (49/49/2), preferably in a ratio of about 10%. The most favourable adhesion properties are obtained when a subbing layer as described above provided with an additional primer layer containing gelatin (preferably 0.25–0.35 g/m$^2$), Kieselsol 300 F (0.30–0.40 g/m$^2$) and a matting agent on the base of polymethylmethacrylate (average size 2 à 3 mm) at a coverage of about 0.001 g/m$^2$.

The silver halide emulsion or mixture of emulsions of the photographic material in connection with the present invention can be incorporated in one single layer but, alternatively, a double emulsion layer or even a multiple layer pack can be applied.

The halide composition of the silver halide emulsions used in accordance with the present invention is not specifically limited and may be any composition selected from e.g. silver chloride, silver bromide, silver iodide, silver chlorobromide, silver bromoiodide, and silver chlorobromoiodide. In a prefered embodiment however, the photographic material is a graphic arts material, most preferably, a graphic arts recording material, which by definition is suited for the recording of screened images, linework and/or text, and/or printed circuit board patterns, electronically stored in an image-setter or scanner. Graphic arts recording materials preferably use emulsions containing a majority of chloride, preferably between 50 mole % and 95 mole %, most preferably between 64 mole % and 90 mole %, and a low amount of iodide, the remaining halide being bromide.

The photographic emulsion(s) can be prepared from soluble silver salts and soluble halides according to different methods as described e.g. by P. Glafkidés in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). They can be prepared by mixing the halide and silver solutions in partially or fully controlled conditions of temperature, concentrations, sequence of addition, and rates of addition. The silver halide can be precipitated according to the single-jet method, the double-jet method, the conversion method or an alternation of these different methods.

The silver halide particles of the photographic emulsion (s) may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

The silver halide grains may have a multilayered grain structure. According to a simple embodiment the grains may comprise a core and a shell, which may have different halide compositions and/or may have undergone different modifications such as the addition of dopes. Besides having a differently composed core and shell the silver halide grains may also comprise different phases inbetween.

Two or more types of silver halide emulsions that have been prepared differently can be mixed for forming a photographic emulsion for use in accordance with the present invention.

The average size of the silver halide grains may range from 0.05 to 1.0 micron, preferably from 0.2 to 0.5 micron. The size distribution of the silver halide particles can be homodisperse or heterodisperse.

The silver halide emulsions can be doped with various metal salts or complexes such as Rhodium and Iridium dopants.

The emulsion can be desalted in the usual ways e.g. by dialysis, by flocculation and re-dispersing, or by ultrafiltration.

The light-sensitive silver halide emulsions are preferably chemically sensitized as described e.g. in the above-mentioned "Chimie et Physique Photographique" by P. Glafkidés, in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners, gold-selenium ripeners or by means of reductors e.g. tin compounds as described in GB 789,823, amines, hydrazine derivatives, formamidinesulphinic acids, and silane compounds. Chemical sensitization can also be performed with small amounts of Ir, Rh, Ru, Pb, Cd, Hg, Tl, Pd, Pt, or Au. One of these chemical sensitization methods or a combination thereof can be used.

The light-sensitive silver halide emulsions can be spectrally sensitized with proper dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes.

The silver halide emulsion(s) for use in accordance with the present invention may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion. Suitable examples are e.g. the heterocyclic nitrogen-containing compounds such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2–58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. Other compounds that can be used as fog-inhibiting compounds are metal salts such as e.g. mercury or cadmium salts and the compounds described in Research Disclosure No. 17643 (1978), Chapter VI.

The fog-inhibiting agents or stabilizers can be added to the silver halide emulsion prior to, during, or after the ripening thereof and mixtures of two or more of these compounds can be used.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl pyrrolidone, polyvinyl imidazole, polyvinyl pyrazole, polyacrylamide, polyacrylic acid, and derivatives thereof, in particular copolymers thereof. Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic material of the present invention may further comprise various kinds of surface-active agents in the photographic emulsion layer or in another hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Other suitable surfactants include perfluorinated compounds. Such surface-active agents can be used for various purposes e.g. as coating aids, as compounds preventing electric charges, as compounds improving slidability, as compounds facilitating dispersive emulsification, as compounds preventing or reducing adhesion, and as compounds improving the photographic characteristics e.g. higher contrast, sensitization, and development acceleration.

Beside the light sensitive emulsion layer(s) the photographic material can contain several non light sensitive layers, e.g. an anti-stress top layer, one or more backing layers, and one or more intermediate layers eventually containing filter- or antihalation dyes that absorb scattering light and thus promote the image sharpness. Suitable light-absorbing dyes are described in i.a. U.S. Pat. Nos. 4,092, 168, 4,311,787 and DE 2,453,217. One or more backing layers can be provided at the non-light sensitive side of the support. This layers which can serve as anti-curl layer can contain i.a. matting agents e.g. silica particles, lubricants, antistatic agents, light absorbing dyes, opacifying agents, e.g. titanium oxide and the usual ingredients like hardeners and wetting agents.

The backing layer(s) may further contain an antistatic agent. Suitable antistatic polymers for incorporation in a backing layer are disclosed in e.g. Research Disclosure, April 1990, Item 31237. Further references on ionic conductive polymers include U.S. Pat. Nos. 4,585,730, 4,701, 403, 4,589, 570, 5,045,441, EP-A-391 402 and EP-A-420 226. An antistatic agent can also be incorporated in a separate layer or in a subbing layer. Relatively recently electrically conducting conjugated polymers have been developed that have electronic conductivity. For ecological reasons the coating of antistatic layers should proceed where possible from aqueous solutions by using as few as possible organic solvents. The production of antistatic coatings from aqueous coating compositions being dispersions of polythiophenes in the presence of polyanions is described in EP 0 440 957.

The photographic elements in connection with the present invention may further comprise various other additives such as e.g. compounds improving the dimensional stability of the photographic element, UV-absorbers, spacing agents and plasticizers.

Suitable additives for improving the dimensional stability of the photographic elements are e.g. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, α-β-unsaturated dicarboxylic acids, hydroxyalkyl (meth)acrylates, sulphoalkyl (meth)acrylates, and styrene sulphonic acids.

Spacing agents can be present, preferably in the top protective layer. In general the average particle size of such spacing agents is comprised between 0.2 and 10 micron. They can be soluble or insoluble in alkali. Alkali-insoluble spacing agents usually remain permanently in the photographic element, whereas alkali-soluble spacing agents usually are removed therefrom in an alkaline processing bath. Suitable spacing agents can be made e.g. of poly (methylmethacrylate), of copolymers of acrylic acid and methylmethacrylate, and of hydroxypropylmethyl cellulose hexahydrophthalate. Other suitable spacing agents have been described in U.S. Pat. No. 4,614,708.

The photographic materials according to the present invention can, after proper exposure, be processed by any means or any chemicals known in the art depending on their particular application. Conventionally, they can be processed in so-called "Rapid Access" chemicals, comprising a conventional Phenidone/hydroquinone or p.-aminophenol/hydroquinone developing solution. However, in a preferred embodiment of the present invention they are processed in a developer which contains an ascordic acid developing agent and which is substantially free of hydroquinone. A much preferred ascorbic acid developing agent is sodium erythrbate.

Their is no need for special "hard dot Rapid Access" developers, although in principle the materials of the present invention can be developed therein.

The development time is usually between 10 and 30 seconds at a temperature of about 35° C. After development the photographic elements of the present invention are preferably fixed in a conventional sodium- or ammonium thiosulphate containing fixing solution.

The present invention will now be illustrated by the following examples without however being limited thereto.

EXAMPLES

Example 1

Preparation of the Emulsion

To an aqueous gelatin solution containing sodium chloride, an aqueous solution of silver nitrate and an aqueous halide solution containing ammonium bromide, sodium chloride, $2.3 \times 10^{-7}$ mol/mol silver of $Na_3RhCl_6$ and $3.0 \times 10^{-7}$ mol/mol silver of $Na_2IrCl_6$ were added with stirring in accordance with a double jet method to form silver chlorobromide grains having an average grain size of 0.27 μm (variation coefficient: 19%) and a chloride content of 64 mol %.

Thereafter, the emulsion was washed using a conventional flocculation method, and then redispersed with 27 g/mol silver of gelatin. The resulting emulsion was adjusted to pH 5.0 and then chemically sensitized at 50° C. by adding 3.9 mg/mol silver of chloroauric acid and 3.3 mg/mol silver of sodium thiosulfate and digesting during three hours. The emulsion was stabilized with $8.4 \times 10^{-3}$ mol/mol silver of 4-hydroxy-6-methyl-1,3,3a,7-tetraazaindene, spectrally sensitized with dye D-1 in an amount of $4.0 \times 10^{-4}$ mol/mol silver. The nucleating agents were added as methanol solutions at the level of 1 to $8 \times 10^{-3}$ mol/mol silver.

Dye D-1

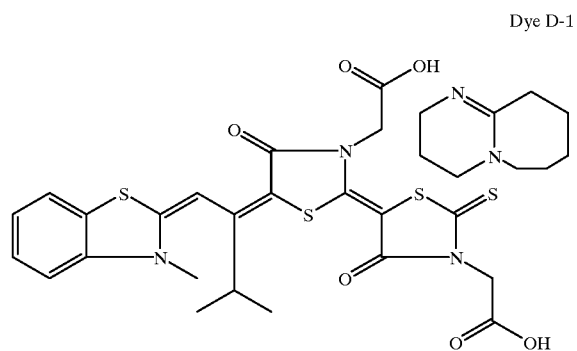

Preparation of Photographic Samples

The emulsions were coated onto a polyethylene terephthalate film support at 4 g per square meter of silver and were overcoated with an aqueous gelatin anti-abrasion layer containing formaldehyde as hardening agent, 25 mg per square meter of 1-p-carboxy-phenyl-3-pyrazolidone, 2.5 mg per square meter of a fluorine-containing surfactant and 10 mg per square meter of poly(methyl methacrylate) matting agent. After the coating the film samples were dried.

Exposure and Photographic Processing

Each sample was exposed to a xenon flash lamp (light emitting Time: $10^{-5}$ s) through both a step wedge and a filter having its peak at 622 nm, and then developed for 20 seconds at 35° C. with developer A. Thereafter, it was subjected successively to fixation in a conventional ammonium thiosulphate containing fixation bath, washing and drying operations. The processing took place in a Rapiline 66T3 processor (trade mark of Agfa-Gevaert N.V.).

| Composition of developer A | |
| --- | --- |
| Water | 800 ml |
| Potassium carbonate | 29.5 g. |
| Potassium sulfite | 34.1 g. |
| Potasium bromide | 2.4 g. |
| Diethyleneglycol | 14 ml |
| Hydroquinone | 17 g. |
| Sodium erythorbate | 2.5 g. |
| 4-Hydroxymethyl-4-methyl-1-phenyl-3-pyrazolidone | 0.275 g. |
| Methylbenzotriazole | 0.06 g. |
| Water to adjust the volume to | 1 l |
| Sodium hydroxide to adjust the pH to | 10.5 |

Evaluation of Image Contrast

Characteristic for materials with hydrazines the sensitometric curves show at high processings speed a decrease of gradation at high densities compared to the gradation at low densities. This leads to low image quality and low densities in practical exposures on an imagesetter. In our evaluation the gradation (γ) was measured between density 3.0+fog and density 3.8+fog. The sensitometric data of the samples are represented in Table 1.

TABLE 1

| Nucleator* | Concentration (mmole/mole Ag) | Fog | γ | Note |
|---|---|---|---|---|
| Compound I | 1.0 | 0.03 | 13.3 | Comparison |
| Compound I | 1.25 | 0.03 | 15.9 | Comparison |
| Compound II | 1.25 | 0.03 | 11.1 | Comparison |
| Compound II | 1.5 | 0.03 | 14.9 | Comparison |
| Compound 1 | 1.0 | 0.03 | 17.9 | Invention |
| Compound 1 | 2.0 | 0.03 | 21.5 | Invention |
| Compound 2 | 2.0 | 0.03 | 21.6 | Invention |
| Compound 3 | 2.0 | 0.03 | 29.5 | Invention |

*the comparison compounds I and II are disclosed in pending European application appl. No. 99203010, cited above. They are represented by following chemical formulas:

compound I:

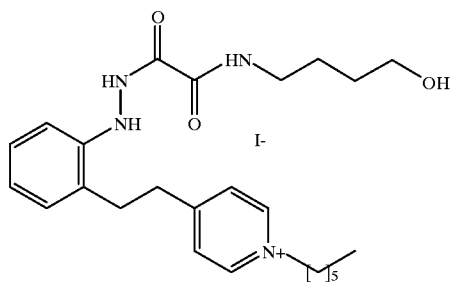

compound II:

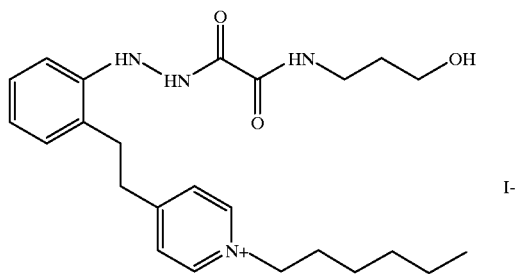

*: the invention compounds are numbered according to the table in the Detailed Description section.

The samples containing the compounds of the present invention clearly show an important increase in contrast at high processing speed for the same concentration (??) leading to enhanced image quality for graphic applications.

Evaluation of the Dot Quality

The samples were exposed on a Red laser diode Image setter Accuset 1000 (Agfa) leading to a 50%-dot pattern after developing in developer A for 40 s at 35° C. and for 25 s at 35° C., fixing, washing and drying in a Rapiline 66T3 processor. The decrease in density between the samples developed at 40 s and 25 s was measured and is summarized in table 2. The dot quality was evaluated with a magnifying glass in order to examine them for definition and smoothness. The quality was expressed as a value ranging from 1 to 5 on an arbitrary qualitative scale. Grade 1 represents a poor, fuzzy, continuous tone type dot. Grade 5 represents an excellent, hard "lith" type dot. The results are summarized in table 2.

TABLE 2

| Nucleator | Concentration (mmole/mole Ag) | Dot quality | Decrease in density | Note |
|---|---|---|---|---|
| Compound II | 1.25 | 1 | 0.32 | Comparison |
| Compound II | 1.5 | 1 | 0.25 | Comparison |
| Compound 1 | 1 | 5 | 0.02 | Invention |
| Compound 1 | 2 | 5 | 0.06 | Invention |
| Compound 3 | 1 | 4 | 0.09 | Invention |
| Compound 3 | 2 | 5 | 0.08 | Invention |

The samples containing the compounds of this invention clearly show, for the same level of fog, a significant higher developer latitude when changing the developing time from 40 s to 25 s, as compared to the film samples containing the comparison compounds.

Example 2

Exposure and Photographic Processing

Each sample from example 1 was exposed to a xenon flash lamp (light emitting time: $10^{-5}$ s) through both a step wedge and a filter having its peak at 622 nm, and then developed for 30 seconds at 35° C. with developer B. Thereafter, it was subjected successively to fixation in a conventional fixation bath, washing and drying operations. The processing took place in a Rapiline 66T3 processor.

| Composition of developer B | |
|---|---|
| Water | 750 ml |
| Potassium hexametaphosphate | 7.5 g. |
| Potassium carbonate | 48.2 g. |
| Potassium sulfite | 3.28 g. |
| Sodium bromide | 6.5 g. |
| Potassium hydroxide | 5.51 g. |
| $Na_4$-EDTA | 2.1 g. |
| Sodium erythorbate | 43 g. |
| Potassium metabisulfite | 21 g. |
| 4-Hydroxymethyl-4-methyl-1-phenyl-3-pyrazolidone | 1.0 g. |
| Rhodafac RM 710 | 75 mg |
| Phenylmercaptotetrazole | 0.03 g. |
| Compound A | 0.035 g. |
| Water to adjust the volume to | 1 l |

Compound A is represented by following formula:

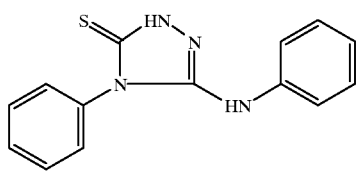

Evaluation of Image Contrast

The samples were exposed on a Red laser diode Image setter Accuset 1000 (Agfa) leading to a 50%-dot pattern after developing in developer B for 30 s at 35° C., fixing, washing and drying in a Rapiline 66T3 processor. The density was measured. The dot quality was evaluated as explained for example 1.

The results are summarized in table 3.

TABLE 3

| Nucleator | Concentration (mmole/mole Ag) | Dot quality | Density at exact rendering of 50%-dot | Sensitivity | Note |
|---|---|---|---|---|---|
| — | 0 | 1 | 3.0 | 100 | |
| Compound I | 1.0 | 2 | 2.22 | 103 | Comparison |
| Compound I | 1.25 | 2 | 2.28 | 102 | Comparison |
| Compound II | 1.5 | 2 | 2.43 | 105 | Comparison |
| Compound 1 | 1 | 5 | 2.87 | 109 | Invention |
| Compound 1 | 2 | 5 | 4.04 | 116 | Invention |
| Compound 3 | 2 | 5 | 4.1 | 112 | Invention |

The samples containing the compounds of this invention clearly show a significant higher practical density, a higher sensitivity and a higher dot quality for the same level of fog in a developing solution containing erythorbic acid as compared to the samples containing the comparison compounds.

What is claimed is:

1. A photographic material comprising a support and at least one silver halide emulsion layer characterized in that said photographic material contains a hydrazine compound represented by following general formula (I):

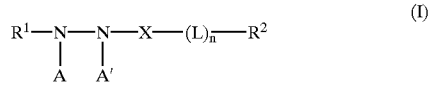

wherein:

$R^1$ is represented by:

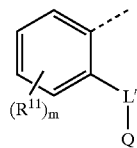

wherein:

$R^{11}$ represents any substituent, m represents an integer from 0 to 4,

L' represents a divalent linking group,

Q represents a cationic aromatic nitrogen containing heterocycle, $R^2$ is selected from the group consisting of a substituted or unsubstituted, saturated or unsaturated aliphatic chain, a substituted or unsubstituted aryl or heteroaryl, with the proviso that $R^2$ comprises a redox moiety, capable of developing an exposed silver halide crystal, X is selected from the group consisting of —CO—, —SO—, —SO$_2$—, —CO—CO—, —P(O)R$^3$, —C(=N—R$^4$), wherein each of $R^3$ and $R^4$ is independently selected from hydrogen, a substituted or unsubstituted, saturated or unsaturated aliphatic chain, a substituted or unsubstituted aryl or heteroaryl, OR$^5$, NR$^6$R$^7$; each of $R^5$ to $R^7$ is selected from the group consisting of hydrogen, a substituted or unsubstituted, saturated or unsaturated aliphatic chain, and a substituted or unsubstituted aryl or heteroaryl, L is a divalent linking group, n=0 or 1, each of A and A' independently represents a hydrogen, a group capable of yielding a hydrogen under alkaline photographic processing conditions or a SO$_2$R$^8$-group provided that if A is SO$_2$R$^8$ A' is a hydrogen and vice versa; $R^8$ is selected from the group consisting of a substituted or unsubstituted, saturated or unsaturated aliphatic chain, a substituted or unsubstituted aryl or heteroaryl.

2. A photographic material according to claim 1 wherein said redox moiety is a hydroquinone moiety or a catechol moiety.

3. A photographic material according to claim 1 wherein said hydrazine compound is incorporated in the silver halide emulsion layer.

4. A photographic material according to claim 1 wherein said hydrazine compound is incorporated in a hydrophilic layer adjacent to the emulsion layer.

5. A method for the preparation of a photographic image comprising the following steps:

(1) exposing image-wise a photographic material comprising a support and at least one silver halide emulsion layer characterized in that said photographic material contains a hydrazine compound represented by following general formula (I):

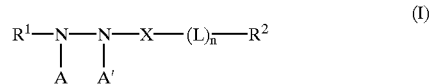

wherein:

$R^1$ represented by:

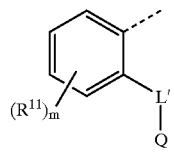

wherein:

$R^{11}$ represents any substituent, m represents an integer from 0 to 4,

L' represents a divalent linking group,

Q represents a cationic aromatic nitrogen containing heterocycle, $R^2$ is selected from the group consisting of a substituted or unsubstituted, saturated or unsaturated aliphatic chain, a substituted or unsubstituted aryl or heteroaryl, with the proviso that $R^2$ comprises a redox moiety, capable of developing an exposed silver halide crystal, X is selected from the group consisting of —CO—, —SO—, —SO$_2$—, —CO—CO—, —P(O)R$_3$, —C(=N—R$^4$), wherein each of $R^3$ and $R^4$ is independently selected from hydrogen, a substituted or unsubstituted, saturated or unsaturated aliphatic chain, a substituted or unsubstituted aryl or heteroaryl, OR$^5$, NR$^6$R$^7$; each of $R^5$ to $R^7$ is selected from the group consisting of hydrogen, a substituted or unsubstituted, saturated or unsaturated aliphatic chain, and a substituted or unsubstituted aryl or heteroaryl, L is a divalent linking group, n=0 or 1, each of A and A' independently represents a hydrogen, a group capable of yielding a hydrogen under alkaline photographic processing conditions or a $SO_2R^8$-group provided that if A is $SO_2R^8$ A' is a hydrogen and vice versa; $R^8$ is selected from the group consisting of a substituted or unsubstituted, saturated or unsaturated aliphatic chain, a substituted or unsubstituted aryl or heteroaryl, (2) developing said exposed photographic material in a developer containing an ascorbic acid developing agent.

* * * * *

UNITED STATES PATENT AND TRADEMARK OFFICE
CERTIFICATE OF CORRECTION

PATENT NO. : 6,566,034 B2
DATED : May 20, 2003
INVENTOR(S) : Johan Loccufier and Stefan Lingier It is certified that error appears in the above-identified patent and that said Letters Patent is hereby corrected as shown below:

<u>Title page,</u>
Item [30], Foreign Application Priority Data, change "00203065" to -- 00203140.9 --.

Signed and Sealed this

Twenty-third Day of September, 2003

JAMES E. ROGAN
*Director of the United States Patent and Trademark Office*